United States Patent
Soenksen et al.

(10) Patent No.: US 11,657,370 B2
(45) Date of Patent: May 23, 2023

(54) MEDICAL IMAGE BASED COLLABORATION

(71) Applicant: LEICA BIOSYSTEMS IMAGING, INC., Vista, CA (US)

(72) Inventors: Dirk Soenksen, Vista, CA (US); Mark Wrenn, Vista, CA (US); Zoya Volynskaya, Vista, CA (US)

(73) Assignee: Leica Biosystems Imaging, Inc., Vista, CA (US)

( * ) Notice: Subject to any disclaimer, the term of this patent is extended or adjusted under 35 U.S.C. 154(b) by 290 days.

(21) Appl. No.: 17/001,413

(22) Filed: Aug. 24, 2020

(65) Prior Publication Data

US 2020/0388375 A1 Dec. 10, 2020

Related U.S. Application Data

(63) Continuation of application No. 14/432,178, filed as application No. PCT/US2013/032583 on Mar. 15, 2013, now Pat. No. 10,754,923.

(Continued)

(51) Int. Cl.
*G16H 30/20* (2018.01)
*G06Q 10/101* (2023.01)
(Continued)

(52) U.S. Cl.
CPC .......... *G06Q 10/101* (2013.01); *G06Q 10/10* (2013.01); *G06Q 50/22* (2013.01); *G16H 30/20* (2018.01); *G16H 40/67* (2018.01); *G16H 80/00* (2018.01)

(58) Field of Classification Search
CPC ....... G06G 10/101; G06G 10/10; G06G 50/22
See application file for complete search history.

(56) References Cited

U.S. PATENT DOCUMENTS

| 10,754,923 B2 | 8/2020 | Soenksen et al. |
| 2002/0061127 A1* | 5/2002 | Bacus ............... G01N 15/1475 382/128 |

(Continued)

FOREIGN PATENT DOCUMENTS

| EP | 2484275 A1 | 8/2012 |
| JP | 2002-056088 A | 2/2002 |

(Continued)

OTHER PUBLICATIONS

Extended European Search Report dated May 20, 2016, for Application No. 13841374.5, 10 pages.

(Continued)

*Primary Examiner* — Robert A Sorey
*Assistant Examiner* — Kristine K Rapillo
(74) *Attorney, Agent, or Firm* — Frost Brown Todd LLP

(57) ABSTRACT

Medical image based collaboration system and methods are provided. A collaboration server 40 creates a medical image based case in response to a request from a requesting system 10 and populates the case with the minimum required information comprising at least a digital medical image and a case number. The collaboration server 40 provides the medical image based case to a consulting system 30 and receives analysis information in response. The collaboration server 40 stores the analysis information in association with the medical image based case and provides the analysis information to the consulting system 30 to complete the medical image based collaboration.

18 Claims, 4 Drawing Sheets

Related U.S. Application Data

(60) Provisional application No. 61/706,466, filed on Sep. 27, 2012.

(51) Int. Cl.
    *G16H 80/00*     (2018.01)
    *G06Q 10/10*     (2023.01)
    *G16H 40/67*     (2018.01)
    *G06Q 50/22*     (2018.01)

(56) References Cited

U.S. PATENT DOCUMENTS

| | | | |
|---|---|---|---|
| 2006/0159325 A1 | 7/2006 | Zeineh et al. | |
| 2006/0159367 A1 | 7/2006 | Zeineh et al. | |
| 2008/0247676 A1* | 10/2008 | Minakuchi | G16H 15/00 382/305 |
| 2009/0274384 A1* | 11/2009 | Jakobovits | G06F 16/51 382/254 |
| 2009/0319291 A1 | 12/2009 | Noordvyk et al. | |
| 2011/0060766 A1 | 3/2011 | Ehlke et al. | |
| 2012/0072452 A1* | 3/2012 | Stratman | G06Q 10/06 707/E17.014 |
| 2012/0183191 A1 | 7/2012 | Nakamura | |
| 2012/0191793 A1 | 7/2012 | Jakobovits | |

FOREIGN PATENT DOCUMENTS

| | | |
|---|---|---|
| JP | 2002-0016289 A | 3/2002 |
| JP | 2008-535528 A | 9/2008 |
| JP | 2009-075760 A | 4/2009 |
| JP | 2009-076024 A | 4/2009 |
| JP | 2011-092682 A | 5/2011 |
| JP | 2011-181015 A | 9/2011 |
| JP | 2015-535998 A | 12/2015 |
| WO | WO 2014/051696 A1 | 4/2014 |

OTHER PUBLICATIONS

European Communication dated Nov. 15, 2017, for Application No. 13841374.5, 10 pages.
European Communication dated May 27, 2019, for Application No. 13841374.5, 5 pages.
International Search Report and Written Opinion dated Jul. 25, 2013, for International Application No. PCT/US2013/032583, 17 pages.
Japanese Notification of Reasons for Refusal dated Mar. 7, 2017, for Application No. 2015-534462, 9 pages.
Japanese Notification of Reasons for Refusal dated Sep. 19, 2017, for Application No. 2015-534462, 5 pages.
Japanese Notification of Reasons for Refusal dated Apr. 2, 2019, for Application No. 2018-007344, 8 pages.

\* cited by examiner

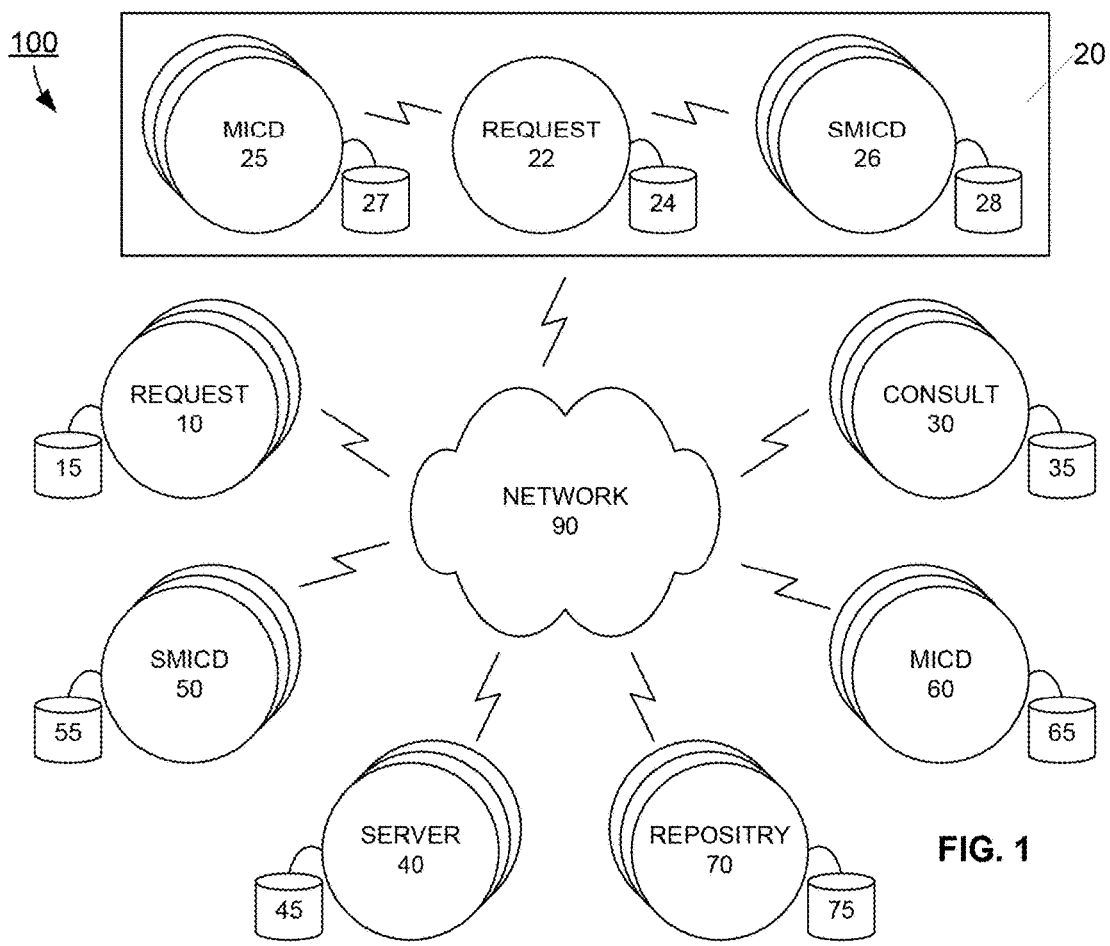
FIG. 1
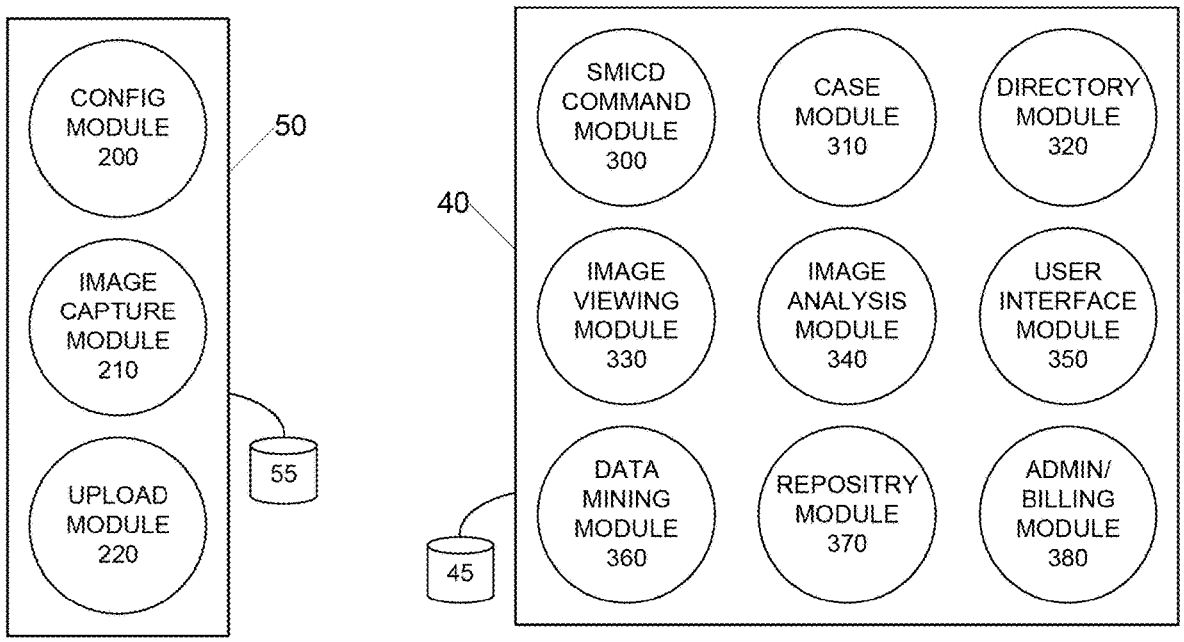
FIG. 2
FIG. 3

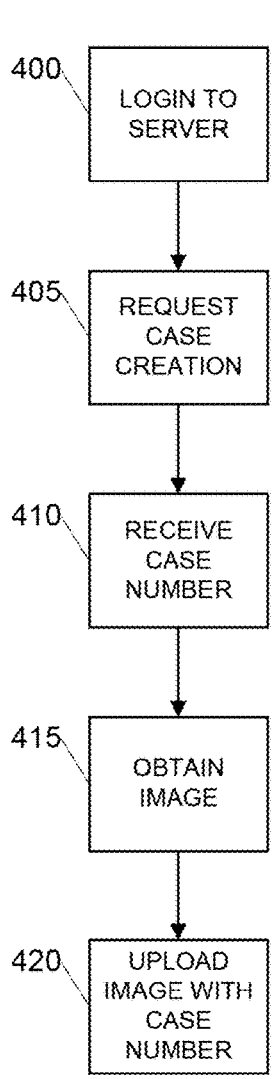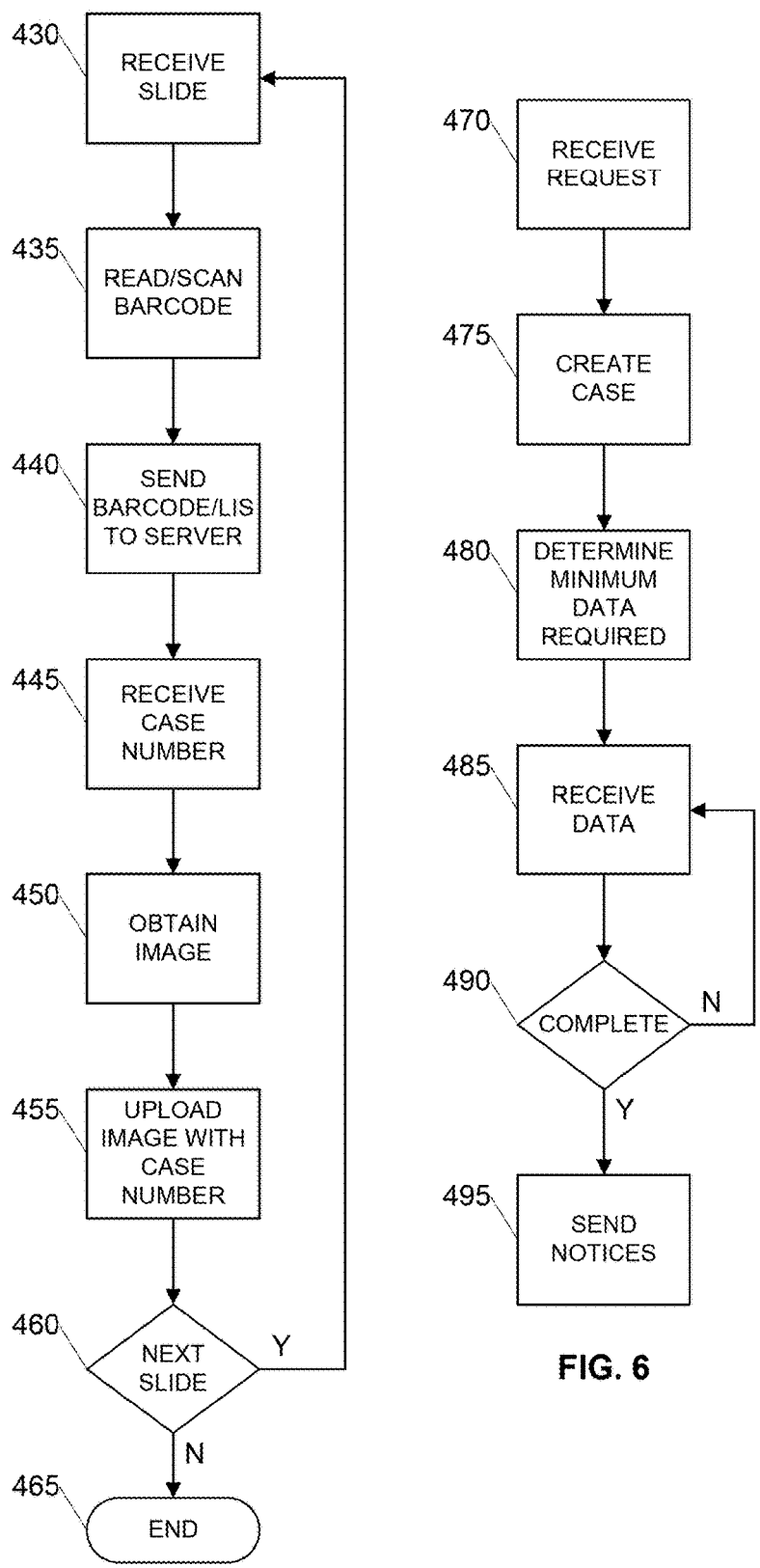
FIG. 4
FIG. 5
FIG. 6

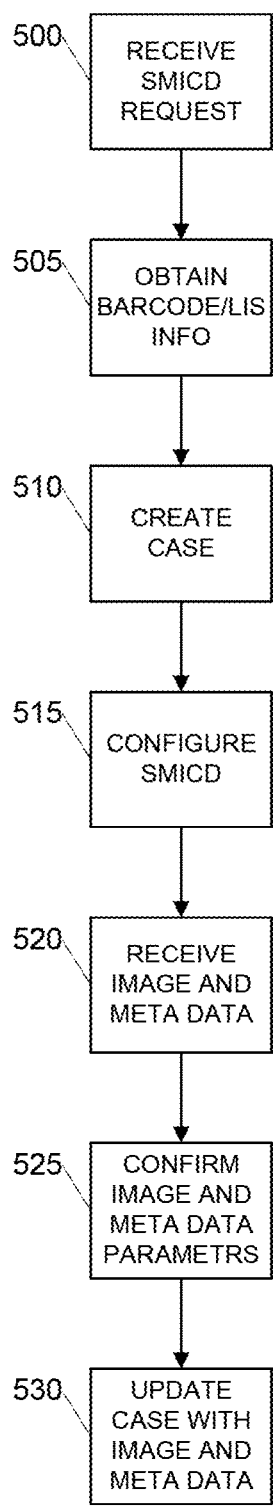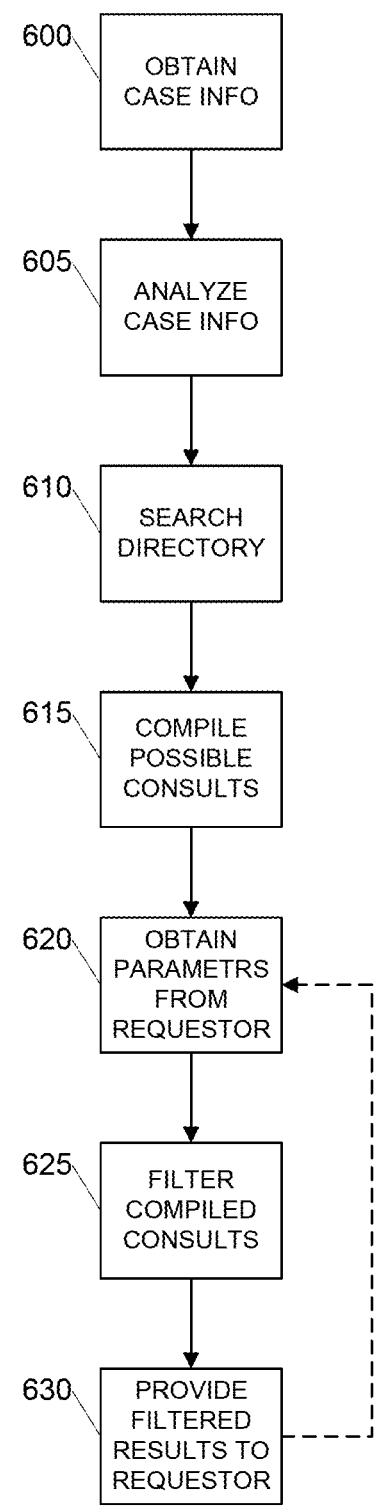
FIG. 7                    FIG. 8

MEDICAL IMAGE BASED COLLABORATION

RELATED APPLICATION

The present application is a continuation of U.S. patent application Ser. No. 14/432,178, filed on Mar. 27, 2015, which is a national stage entry of International Patent Application No. PCT/US2013/032583, filed on Mar. 15, 2013, which claims priority to U.S. Provisional Patent Application No. 61/706,466, filed on Sep. 27, 2012, which are all hereby incorporated herein by reference as if set forth in full.

BACKGROUND

Field of the Invention

The present invention generally relates to collaboration surrounding medical images and more specifically relates to primary diagnoses, secondary opinions, and collaboration between professionals facilitated by medical images.

Related Art

In conventional medical image based cases, an individual medical professional may feel uncomfortable rendering a final diagnosis on a difficult case and/or a case outside his or her area of expertise. Such a medical professional may want to consult with a peer or a recognized expert in the particular subject matter of the medical image based case. Similarly, a medical practice group or hospital or health care company may desire to consolidate its diagnoses for medical image based cases. Such consolidation may be within the medical group or hospital or health care company or may be external to the medical group or hospital or health care company. Conventional systems based upon glass microscope slides or proprietary medical imaging systems fail to allow easy, scalable and reliable collaboration on medical image based cases. Digital imaging for medical image based cases holds the promise of allowing some level of collaboration but has not been able to overcome the significant technical and administrative challenges associated with medical image based collaboration. Therefore, what is needed is a system and method that provides for easy, scalable and reliable medical based image collaboration to meet the needs of individual medical professionals while also meeting the needs of medical groups and hospitals and health care companies and the like.

SUMMARY

Accordingly, a medical image based collaboration system is described herein that provides easy, scalable and reliable solutions to the problems described above. The system includes a collaboration server that creates a medical image based case and establishes a set of minimum required information to complete the case. The collaboration server creates the medical image based case in response to a request from a requesting system and the collaboration server cooperates with the requesting system to populate the medical image based case with at least a digital medical image and a case number to complete the case. The collaboration server provides the medical image based case to a consulting system and receives analysis information in response. The collaboration server stores the analysis information in association with the medical image based case and provides the analysis information to the consulting system to complete the medical image based collaboration.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIG. 1 is a network diagram illustrating an example system for medical image based collaboration according to an embodiment of the invention;

FIG. 2 is a block diagram illustrating an example smart medical image capture device in a system for medical image based collaboration according to an embodiment of the invention;

FIG. 3 is a block diagram illustrating an example server in a system for medical image based collaboration according to an embodiment of the invention;

FIG. 4 is a flow diagram illustrating an example process for initiating medical image based collaboration by a requesting system according to an embodiment of the invention;

FIG. 5 is a flow diagram illustrating an example process for automatically initiating medical image based collaboration by a smart medical image capture device according to an embodiment of the invention;

FIG. 6 is a flow diagram illustrating an example process for creating a complete medical image based case according to an embodiment of the invention;

FIG. 7 is a flow diagram illustrating an example process for configuring a smart medical image capture device in accordance with medical image based case parameters according to an embodiment of the invention;

FIG. 8 is a flow diagram illustrating an example process for searching a directory of consulting systems according to an embodiment of the invention;

DETAILED DESCRIPTION

Figure 9:
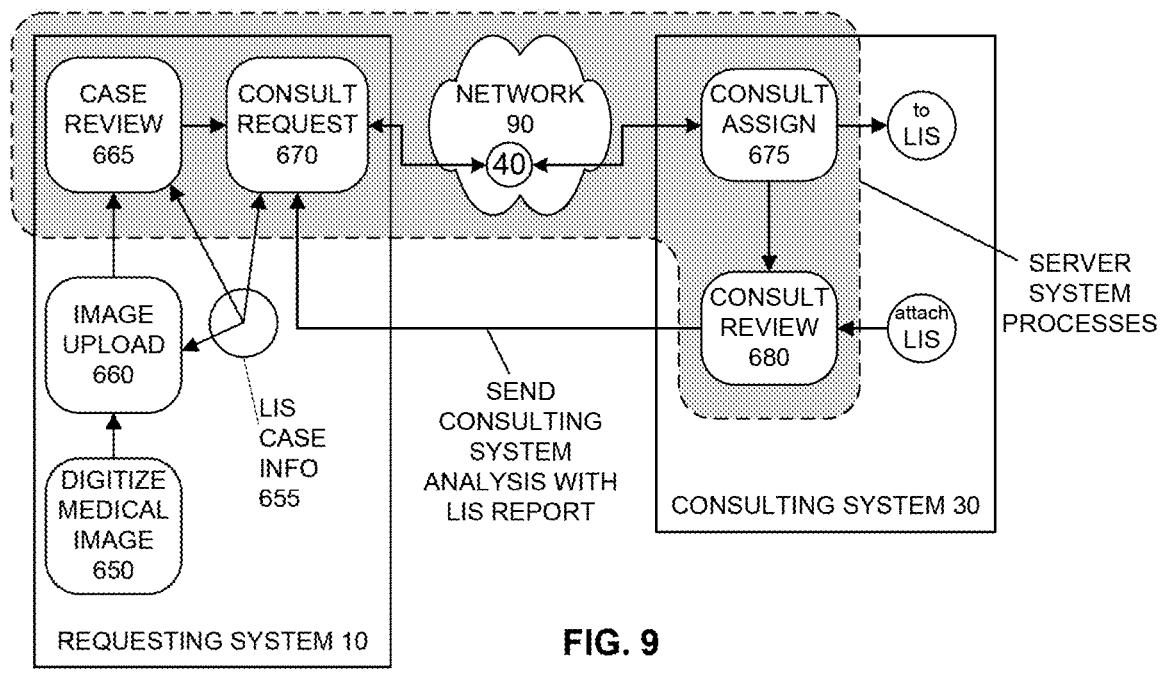
FIG. 9 is a block diagram illustrating an example workflow in a system for medical image based collaboration according to an embodiment of the invention.

Certain embodiments disclosed herein provide for medical imaging based collaboration. For example, one method disclosed herein allows for a requesting system to cooperate with a collaboration server system to create a medical image based case on the server, establish a minimum data set required to complete the case, provide the completed case to a consulting system, update the case with analysis information from the consulting system and receive the updated case from the server system. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

FIG. 1 is a network diagram illustrating an example system 100 for medical image based collaboration according to an embodiment of the invention. In the illustrated embodiment, the system 100 comprises a network 90 that communicatively couples a plurality of entities. It should be noted that an entity may be an organization such as a company or a medical practice group or it may be one or more computer server device or one or more medical image capture devices or the like. Throughout this description, entities may be alternatively referred to as systems or institutions or the like.

In the illustrated embodiment, the network 90 communicatively couples one or more requesting systems 10 and 20, one or more consulting systems 30, one or more collaboration servers 40, one or more smart medical image capture systems 50, one or more medical image capture systems 60 and one or more repository systems 70. As shown in FIG. 1, each of these systems has one or more data storage areas 15, 24, 27, 28, 35, 45, 55, 65 and 75, which may include both persistent and volatile storage. The network 90 can be a public or private network, a wired or wireless network or any combination including public and private and wired and wireless. Network 90 can include a personal area network ("PAN"), a local area network ("LAN"), a wide area network ("WAN"), or a distributed combination of networks collectively comprising a global communications network such as the Internet. Network 90 can be an ad hoc network or a persistent network and can be fixed in location, be mobile, or network 90 may comprise a combination of fixed and mobile components. Additionally, network 90 may carry communications corresponding to a single network protocol or corresponding to multiple network protocols.

Requesting system 10 is configured to interface with the server 40 to initiate the creation of one or more medical image based cases and facilitate the completion of such cases. Requesting system 10 may include one or more computer devices capable of autonomous operation to accomplish the above described creation and completion of medical image based cases. In one embodiment, the requesting system 10 is a hospital or medical practice group with one or more professionals tasked with rendering diagnoses based in part on medical images. The requesting system 10 may or may not include one or more smart medical image capture devices ("SMICD") and other medical image capture devices.

For example, in one embodiment, a medical practice group 20 comprises a requesting system 22 and one or more smart medical image capture devices 26 and one or more other medical image capture devices 25. In such an embodiment, the group 20 may also include a laboratory information system ("LIS")—not separately illustrated in FIG. 1—and other systems—also not shown in FIG. 1—that store information related to a medical image based case.

In an alternative embodiment, requesting system 10 operates over network 90 in cooperation with one or more smart medical image capture devices 50 and/or one or more other medical image capture devices 60. In one embodiment, the difference between a smart medical image capture device 50 and a medical image capture device 60 is that the smart medical image capture device 50 is configured to interface with the one or more collaboration servers 40 to initiate the creation of one or more medical image based cases and facilitate the completion of such cases. Both the smart medical image capture device 50 and the medical image capture device 60 are capable of storing the digital medical images they capture. Otherwise, the one or more smart medical image capture devices 50 and the one or more medical image capture devices 60 are devices that are capable of capturing and storing medical images. Some examples of such devices include digital pathology systems, magnetic resonance imaging ("MRI") systems, computed axial tomography ("CAT") systems, and X-ray systems just to name a few. Other medical imaging systems may also be employed in the system 100 as will be understood by those skilled in the art.

In one embodiment, the repository 70 is configured to store medical image based cases and provide decision support to professionals as requested for medical image based diagnoses. The repository 70 can also advantageously store important collections of medical images for training and educational purposes.

Collaboration server 40 is configured to interface with requesting systems 10 and 20, consulting systems 30, smart medical image capture devices 50, medical image capture devices 60, and repositories 70 to implement and facilitate medical image based collaboration. The collaboration server 40 creates and manages medical image based cases and manages the workflow between a requesting system 10 (and any related systems such as the aforementioned LIS) and a consulting system 30 and any smart medical image capture devices 50 and the repository 70. It should be noted that a medical image based case is an electronically stored data set that comprises at least a medical image and an identifier referred to herein as a case number.

In operation, the system 100 is configured such that the requesting system 10 initially requests that a medical image based case be created by the collaboration server 40. This can be accomplished by an operator at the requesting system 10 logging into the collaboration server 40 and submitting the request. This can also be accomplished by a smart medical image capture device 50 sending an electronic request communication to the collaboration server 40 over the network 90. The collaboration server 40 cooperates with the requesting system 10 (operator or SMICD) to create the case and define the minimum data set required for the case to be complete. The collaboration server 40 and/or the requesting system 10 then cooperate to provide the collaboration server 40 with the necessary information for the case to be complete and the collaboration server 40 stores the case in a local or remote data storage area accessible by the collaboration server 40.

Once the case is completed, the collaboration server 40 provides notice to the consulting system 30 (e.g., by sending an electronic notice communication to the consulting system 30 over the network 90) and the consulting system 30 is allowed to access the medical image based case on the server 40. In one embodiment, the collaboration server 40 provides the medical image based case information to the consulting system 30 via the network 90 in response to one or more requests for the information and none of the medical image based case information is persistently stored in a data storage area the consulting system 30.

The consulting system 30 is configured to provide the collaboration server 40 with analysis information based on the provided medical image based case information and the collaboration server 40 is configured to receive that information and store that information in association with or as part of the medical image based case. The collaboration server 40 can then send a notice to the requesting system 10 and provide the analysis information to the requesting system 10, for example via the network 90 in response to one or more requests for the analysis information from the requesting system 10.

For example, in one embodiment, the collaboration server 40 creates a medical image based case and receives first medical image based case information comprising a digital medical image from the requesting system 10. The collaboration server 40 assigns a case number and with the case number and the digital medical image, the medical image based case is considered complete. The collaboration server 40 notifies the consulting system 30 and provides the medical image based case information to the consulting system 30 and receives analysis information in response. The collaboration server 40 stores the analysis information as part of or in association with the medical image based case and notifies the requesting system 10 that the analysis information is available for review. The collaboration server 40 provides the analysis information to the requesting system 30 to complete the medical image based collaboration. The collaboration server 40 may also transmit the medical image based case to the repository 70 if the medical image based case meets certain predetermined criteria for inclusion in the repository 70.

FIG. 2 is a block diagram illustrating an example smart medical image capture device 50 in a system for medical image based collaboration according to an embodiment of the invention. In the illustrated embodiment, the SMICD 50 comprises a configuration module 200, an image capture module 210 and an upload module 220. The SMICD 50 also has a data storage area 55, which may include both persistent and volatile storage as described above.

The configuration module 200 is configured to establish the parameters under which the SMICD 50 will capture medical image data. For example, in a microscope based imaging system, the configuration module 200 may set a parameter that determines the magnification at which the system will capture image data. Alternatively, in an MRI system, the configuration module 200 may set a parameter that determines the frequency of image slices captured. A variety of image capture parameters can be established by the configuration module 200 as will be understood by those skilled in the art. Advantageously, the one embodiment, the configuration module 200 is configures to cooperate with the collaboration server 40 to establish these parameters. This allows the collaboration server 40 to ensure that appropriate medical image data is made part of the medical image based case. For example, for certain tissue types or for certain disease types, image data may need to be captured as a certain magnification. The configuration module 200 operates to cooperate with the collaboration server 40 to set a parameter on the SMICD 50 that will cause the digital medical image data to be captured at the desired magnification.

The image capture module 210 is configured to capture and store digital medical image data as appropriate for the particular type of SMICD 50, e.g., digital pathology system, MRI system, CT system, X-ray system, etc.

The upload module 220 is configured to cooperate with the collaboration server 40 to securely upload digital medical image data to the collaboration server 40. For example, the upload module 220 may encrypt the medical image data prior to sending the medical image data to the collaboration server 40. Additionally, the upload module 220 may use a secure data communication protocol to send the encrypted medical image data to the collaboration server 40.

In addition to sending the digital medical image data to the collaboration server 40, the upload module 220 may also send metadata and other information to the collaboration server 40. For example, the upload module 220 may also provide the collaboration server 40 with information from multiple sources such as an LIS, other imaging systems (e.g., a digital camera that captures a gross image), reports such as radiology reports, pharmacy reports, patient information, patient prescription information, patient insurance information, requesting system billing information, ancillary test results (e.g, immunohistochemistry, flow cytometry, special stains information, genetics information, etc.), LIS information, requesting system 10 case identification information, requesting system 10 preferred consulting system information, and any other information maintained by the requesting system 10.

In an alternative embodiment, such additional information is provided to the collaboration server 40 by another device that is part of the requesting system 10 and not by the SMICD 50, which may for example be a specialized medical imaging device that is unable to host and execute the upload module 220.

FIG. 3 is a block diagram illustrating an example collaboration server 40 in a system for medical image based collaboration according to an embodiment of the invention. In the illustrated embodiment, the server 40 comprises SMICD command module 300, a case module 310, a directory module 320, an image viewing module 330, an image analysis module 340, a user interface module 350, a data mining module 360, a repository module 370 and an admin/billing module 380. The collaboration server 40 also has a data storage area 45, which may include both persistent and volatile storage as described above.

SMICD command module 300 is configured to interface via network 90 with the configuration module 200 and the upload module 220 of the SMICD 50. The SMICD command module 300 is configured to provide information and instructions to the SMICD 50 and to receive requests and information from the SMICD 50. In one embodiment, the SMICD command module 300 coordinates the workflow for medical image based collaboration in cooperation the various other modules on the collaboration server 40. For example, the command module 300 may cooperate with the case module 310 to create and complete a medical image based case, may cooperate with the directory module 320 to allow a requesting system to search the directory of available consulting systems (individuals and groups), may cooperate with the image viewing module 330 to provide medical image based case information to a consulting system, cooperate with the image analysis module 340 and the case module 310 to update a medical image based case with image analysis information, cooperate with the user interface module 350 to provide information on the display of a user device or a viewing device, cooperate with the data mining module 360 to analyze medical image based information to identify trends in data and provide other analytical information based on such analyses, cooperate with the repository module 370 to archive medical image based case information for later use, and cooperate with the admin/billing module 380 to effect payment for medical image based collaboration and provide reports to both consulting systems and requesting systems.

In one embodiment, the SMICD command module 300 receives an electronic request from a requesting system 10 to create a medical image based case. The request may be received from an operator of a computer device at the requesting system 10 or it may be received directly from a SMICD 50. In response, the command module 300 creates a medical image based case and establishes a minimum data set required to complete the case. In one embodiment, the minimum data set is a digital medical image and a case number. The command module 300 is configured to assign a case number to the medical image based case. In one embodiment the case number may include a portion that is associated with an LIS system employed by the requesting system. The command module 300 can request additional information that is to be made part of the medical image based case, for example by querying the requesting system or by directly querying the LIS system employed by the requesting system. Once the medical image based case is complete, the command module 300 notifies the consulting system and then cooperates with the image viewing module 330 to allow the consulting system to view the medical image based case information, for example via a browser running on a computer system associated with the consulting system.

The command module 300 is also configured to receive medical image based case analysis information from the consulting system and store that information in association with the medical image based case and then to cooperate with the user interface module 350 to provide the medical image based information, including the medical image based case analysis information to the requesting system.

The command module 300 is also configured to receive uploaded medical image data, either in cooperation with an upload module 220 or otherwise. For example, in an embodiment where the requesting system does not use a smart medical image capture device, an operator at the requesting system may login to the collaboration server 40 and interact with the SMICD command module 300 via the user interface module 350 and provide digital medical image data. This may be accomplished by the command module 300 presenting the operator with a file upload window to allow the operator to select a digital medical image file located in a data storage area at the requesting system. Additional and alternative information may also be provided from the requesting system in this fashion and accordingly various reports, gross images, LIS information, ancillary test results and the like can be incorporated into the medical image based case in this fashion.

Case module 310 is configured to create and store medical image based cases and cooperate with the command module 300 to establish a set of minimum required data to complete a medical image based case. For example, in Table 1 below, the case module 300 maintains a set of minimum required information for a plurality of medical conditions and tracks the status of any new medical image based case until the various required elements are included in the case information to allow the medical image based case to be determined to be complete.

| MEDICAL CONDITION | MINIMUM REQUIRED INFORMATION | | | | |
| --- | --- | --- | --- | --- | --- |
| CONDITION_1 | X | | X | | X |
| CONDITION_2 | | X | X | | X |
| CONDITION_3 | | X | | X | X |

Case module 310 may also cooperate with image analysis module 340 to update the medical image based case information to include image analysis information provided by the image analysis module 340. The case module 310 may also maintain a current status of the medical image based case in order to facilitate tracking and management of the workflow associated with the medical image based case. In one embodiment, the current status of the case may include whether the case is pending or complete, whether the consulting system has requested additional information (and if so, who is responsible to provide the additional information). Advantageously, the case module 310 may cooperate with the directory module 320 to maintain a set of preferences for consulting systems that are individuals or groups and then apply those preferences to individual medical image based cases that are associated with the particular consulting systems that are those individuals or groups.

Directory module 320 is configured to maintain in a data storage area a list of consulting systems and their respective availabilities that can be searched by requesting systems in need of a consulting system. As discussed above, the directory module 320 may also maintain preferences of each consulting system so that medical image based cases assigned to a particular consulting system are properly seeded with the information desired by the particular consulting system. This capability advantageously reduces the turn-around-time ("TAT") associated with providing a consultation analyses.

In one embodiment, the directory module 320 may include additional information for each consulting system. For example, in Table 2 below the directory module 320 maintains subspecialty information for each consulting system in addition to a price per case that is charged by the respective consulting system for the particular subspecialty, a turn-around-time and an availability that is expressed as the volume of cases per month that the consulting system can process.

| CONSULTING SYSTEM | SUB-SPECIALTY | PRICE PER CASE | TAT | VOLUME |
| --- | --- | --- | --- | --- |
| CONSULTING_1 | BREAST | $210 | 4D | 40/MO |
| CONSULTING_2 | LUNG | $225 | 2D | 25/MO |
| CONSULTING_3 | PROSTATE | $275 | 3D | 200/MO |

Image viewing module 330 is configured to provide a consulting system or a requesting system with medical image based case information including metadata and digital medical image data. The image viewing module 330 is advantageously capable of presenting such data in a browser window of a consulting system's computer. The image viewing module 330 is also capable of providing this same information to another party such as the requesting party or some other third party with the appropriate access credentials.

Image analysis module 340 is configured to store and execute image analysis algorithms on the medical image based case information in order to provide more robust information and data to the requesting system and the consulting system alike. The image analysis module 340 is also configured to cooperate with the case module 310 to store such image analysis information in association with each medical image based case so analyzed.

The image analysis module 340 may also be employed to analyze digital medical image data that is part of a medical image based case and determine if the digital medical image data is appropriate for the medical image based case. For example, if the particular condition or tissue type that is the subject of the medical image based case requires a digital medical image at a particular resolution, the image analysis module 340 is configured to analyze the digital medical image data and determine if the digital medical image data meets the required parameters for the medical image based case. As discussed above, such parameters may be established in advance of capturing the digital medical image by the SMICD command module 300 in cooperation with the configuration module 200 at the requesting system.

User interface module 350 is configured to present information on a display at the requesting system or the consulting system and receive input and instructions from an operator and provide such input and instructions to, for example, the SMICD command module 300.

Data mining module 360 is configured to analyze medical image based case information stored in the data storage area and identify trends and events to facilitate improved medical image based collaboration by requesting systems and consulting systems. For example, the data mining module 360 can identify major and minor discrepancies based on an analysis of all of the medical image based collaborations for a requesting system. Specifically, the data mining module 360 may compare the analysis information provided to the requesting system by a consulting system for a particular medical condition against the initial diagnosis information that is stored as part of the medical image based case. The data mining module 360 may make this comparison across all medical image based cases for a particular requesting system and calculate a major and minor discrepancy rate.

Advantageously, if the major discrepancy rate for the requesting system is sufficiently low, then the requesting system may be able to reduce future costs by eliminating consultations for the particular medical condition. Similarly, if the major discrepancy rate for the requesting system is sufficiently high then the requesting system may be able to improve accuracy of future diagnoses by requiring consultations in all instances of the particular medical condition.

The data mining module 360 is also configured to identify areas where training could be beneficial for a requesting system or a consulting system and to conduct companion diagnostics image analysis. The data mining module 360 is also configured to analyze information related to rejected image data and provide quality assessments of at least medical imaging services or specimen preparation laboratories.

Repository module 370 is configured to send identified medical image based cases to a repository server for archival and storage and analysis for decision support and educational purposes. The repository module 370 may also interface with an operator via the user interface module 350 to facilitate searching of the repository and facilitate the use of the decision support capabilities of the repository 70 by the operator. Advantageously, the repository module 370 may assist an operator in using certain sophisticated visual search capabilities offered by the repository 70.

Admin/billing module 380 is configured to bill requesting systems for services provided by the collaboration server and/or the consulting system. The admin/billing module 380 is also configured to pay consulting systems for services provided by the consulting systems to the collaboration server 40 and/or the requesting system. The admin/billing module 380 is also configured to provide a robust report generating capability for requesting systems and consulting systems. In one embodiment, the admin/billing module 380 works in cooperation with the data mining module 360 to provide reports and other information including data mining module 360 analysis regarding a requesting system's major and minor discrepancies and/or a consulting system's areas of strength. The admin/billing module 380 can therefore assist a requesting system with identifying areas where its medical professionals may need some future training and assist a consulting system with identifying areas where its medical professionals can market expanded consulting services or training services.

FIG. 4 is a flow diagram illustrating an example process for initiating medical image based collaboration by a requesting system according to an embodiment of the invention. The illustrated process may be carried out by a system such as previously described with respect to FIGS. 1-3. Initially, in step 400 an operator at a requesting system logs into the collaboration server and requests that a case be created in step 405. In response to this request, the collaboration server creates a data structure that resides in a memory of the collaboration server and stores the medical image based case information. The collaboration server assigns a case number to the newly created case and the operator at the requesting system receives the case number in step 410. Next, the operator at the requesting system obtains the digital medical image in step 415, for example, by instructing a digital medical imaging device to capture a digital medical image. Alternatively, if the digital medical image already exists, the operator may simply browse a hierarchical file system (or other type) and select the desired digital medical image. Once the digital medical image has been obtained (by real time image capture or by selecting from a file system), in step 420 the requesting system uploads the digital medical image in association with the case number previously received in step 410.

In this fashion, an operator at a requesting system can effectively create and complete a number of medical image based cases on the collaboration server. In an embodiment where additional information is required to meet the minimum required data to complete a medical image based case, the operator can either upload the additional required information in step 420 or allow the collaboration server to interface with an LIS system or other data source at the requesting system or elsewhere to obtain any additional information needed to complete the medical image based case.

FIG. 5 is a flow diagram illustrating an example process for automatically initiating medical image based collaboration by a smart medical image capture device according to an embodiment of the invention. The illustrated process may be carried out by a system such as previously described with respect to FIGS. 1-3. Initially, in step 430 the SMICD receives a first slide. In this example embodiment, the SMICD is a digital pathology system that is configured with an autoloader having a one hundred and twenty (120) physical glass microscope slide capacity. Accordingly, the SMICD receives a first slide by way of the autoloader and then in step 435 the SMICD scans or reads one or more barcodes that are affixed to the glass microscope slide. As will be understood by those skilled in the art, the one or more barcodes, when decoded, provide access to certain information about the specimen on the glass microscope slide and the patient to which the specimen belongs. For example, the information about the specimen may include what stains the specimen was treated with and the information about the patient may include demographic information, medical record information, LIS information and the like.

Next, in step 440 the SMICD sends an image of the barcode(s), the decoded barcode, or the information corresponding to the barcode to the collaboration server. In turn, the collaboration server creates a medical image based case in step 440 and sends a case number back to the SMICD, as shown in step 445. Next, the SMICD obtains the digital medical image in step 450. In this particular example embodiment, the digital pathology system digitally scans the glass microscope slide to create a whole slide image. Alternatively, the digital pathology system may only digitally scan a portion of the specimen on the slide. Advantageously, any type of digital pathology system that creates a digital image of a specimen on a glass microscope slide may be employed.

Once the digital medical image has been obtained, the image is uploaded to the collaboration server in association with the case number as shown in step 455. In one embodiment, this completes the medical image based case on the collaboration server. If additional information is required to meet the minimum required data for the medical image based case, such data can be provide to or obtained by the collaboration server as previously described.

Continuing with the present example of the digital pathology system SMICD, if the autoloader has additional unscanned slides, as determined in step 460, the SMICD loops back to step 430 and receives another glass microscope slide and the process of creating another medical image based case proceeds. Alternatively, if all 120 glass microscope slides from the autoloader have been scanned and medical image based cases created for each glass microscope slide, then the process ends in step 465.

FIG. 6 is a flow diagram illustrating an example process for creating a complete medical image based case according to an embodiment of the invention. The illustrated process may be carried out by a system such as previously described with respect to FIGS. 1-3. Initially, in step 470 the collaboration server receives a request to create a new medical image based case and then in step 475 the collaboration server creates the medical image based case. Next in step 480 the collaboration server determines the minimum data required to complete the case.

The minimum data required to complete a case may be predicated upon the subject matter of the case. For example, if the medical image based case is of a certain tissue type or a certain pathological condition or the like, then the minimum data required may be established by a predetermined list of requirements that are associated with the particular tissue type, certain pathological condition or the like. The collaboration server may obtain information about the tissue type or pathological condition from LIS information or other metadata information that was provided to the collaboration server in association with the case number. Additionally, the collaboration server may request information including tissue type, pathological condition or the like from one or more data sources at the requesting system or from one or more data sources elsewhere that are not affiliated with the requesting system. For example, industry groups or medical professional groups may establish minimum standards that can be used by the collaboration server as minimum data requirements. In one embodiment, the collaboration server maintains a table of minimum data requirements for a plurality of types of medical image based cases.

Once the minimum data required has been determined and associated with the medical image based case, the collaboration server proceeds to receive data and store the received data as part of, or in association with, the medical image based case as shown in step 485. The collaboration server continues to evaluate whether all of the minimum data required has been received and stored for the medical image based case as indicated by step 490 and the continuing loop between evaluating if the case is complete in step 490 and receiving data in step 485. Once the collaboration server has determined that the medical image based case is complete in step 490, the collaboration server sends a notice to one or more consulting systems that are associated with the medical image based case. Advantageously, the notice indicates that the medical image based case is available for analysis by the one or more consulting systems.

FIG. 7 is a flow diagram illustrating an example process for configuring a smart medical image capture device in accordance with medical image based case parameters according to an embodiment of the invention. The illustrated process may be carried out by a system such as previously described with respect to FIGS. 1-3. Initially, in step 500 the collaboration server receives a request to create a case from an SMICD at a requesting system. Alternatively, the collaboration server may receive the request from an operator at the requesting system where the operator is using a communication device that is not an SMICD. Next, in step 505 the collaboration server obtains certain information for the medical image based case, for example, the collaboration server may receive barcode or LIS or other information directly from the SMICD device or from other data sources. Alternatively, the operator may upload or otherwise provide such information to the collaboration server. Next, in step 510 the collaboration server creates the case and as part of creating the case the collaboration server assigns a case number to the medical image based case. In one embodiment, the case number may be a combination of a requesting system case number and a consulting system case number. Alternatively, the case number may be a combination of a requesting system case number and a collaboration server case number or the case number may be a combination of a requesting entity case number and a consulting system case number and a collaboration server case number. A variety of options for case numbers may be employed, with workflow advantages realized from repurposing the requesting system case number and the consulting system case number.

After the case has been created, the collaboration server configures the SMICD. This configuration of the SMICD can be accomplished by the collaboration server by sending a single command or a series of commands to the SMICD to cause the SMICD to execute the commands and thereby establish the desired parameters for the medical image capture process. In one embodiment, configuring the SMICD establishes the parameters under which the medical imaging process takes place. For example, illumination characteristics, magnification, resolution, speed, frequency, area and other general and/or specific medical imaging characteristics for the particular type of SMICD can be established through the configuration process. Once the SMICD has been configured, the collaboration server receives image data and metadata in step 520 and analyzes the image data and metadata to confirm that the image data corroborates that the digital medical image was captured using the parameters that were established when the SMICD was configured with respect to step 515. If the analysis of the image data confirms that the correct parameters were used, the collaboration server updates the case file with the image data and the metadata received in step 520. Alternatively, if the analysis of the image data confirms or suggests that the correct parameters were not used, the collaboration server can discard the image data and the metadata received in step 520.

In one embodiment, analysis of the image data includes determining the resolution of the digital medical image, determining the magnification of the digital medical image, determining the image quality of the digital medical image, determining the illumination characteristics of the digital medical image, determining if the digital medical image was captured under fluorescent imaging conditions, determining the tissue type of the specimen, determining the color space of the digital medical image and the like.

FIG. 8 is a flow diagram illustrating an example process for searching a directory of consulting systems according to an embodiment of the invention. The illustrated process may be carried out by a system such as previously described with respect to FIGS. 1-3. Initially, in step 600 the collaboration server obtains medical image based case information, e.g., from a data storage area, and analyzes the medical image based case information in step 605. Based on the analysis, in step 610 the collaboration server searches a directory of consulting systems. As previously discussed, a consulting system may be an individual consultant or a group of consultants. Based on the search results, the collaboration server compiles an initial list of possible consulting systems in step 615. In one embodiment, the initial list may be compiled based on a match of the medical image based case type and a consulting system's subspecialty.

Once an initial list has been compiled by the collaboration server, in step 620 the sever obtains additional parameters from the requesting system and filters the compiled list of consulting systems based on the additional parameters, as shown in step 625. Next, in step 630 the collaboration system provides the filtered list of consulting systems to the requesting system. Optionally, the collaboration server may loop back and obtain additional or alternative parameters from the requesting system and then apply the additional or alternative parameters to further filter the initial list of possible consulting systems. This process of reviewing and filtering may continue through multiple iterations until such time as the requesting system is satisfied with the list of available consulting systems.

In one embodiment, the initial compiled list or the filtered list (or both) may be compiled or filtered based on the availability of the consulting system. Accordingly, if a particular consulting system is currently too busy or is currently on vacation, then that particular consulting system may advantageously be excluded from both the initial compiled list and the filtered list.

FIG. 9 is a block diagram illustrating an example workflow in a system for medical image based collaboration according to an embodiment of the invention. The illustrated process may be carried out by a system such as previously described with respect to FIGS. 1-3. In the illustrated embodiment, the system comprises a requesting system 10 communicatively coupled with a consulting system 30 via a collaboration server 40 and a network 90. Initially, in step 650 a medical image is digitized at the requesting system 10 and then uploaded in step 660 to a data storage area at the collaboration server 40. As shown, LIS case information and/or additional information 655 may be provided to the collaboration server 40 at the time of the image upload 660 or during case review 665 or consult request 670.

Once the digital medical image has been uploaded to the server and the medical image based case has been created, the next steps in the workflow are performed at the server 40 in cooperation with the requesting system 10 and/or the consulting system 40. For example, in step 665 the collaboration server 40 facilitates a review of the medical image based case by the requesting system 10 to allow the requesting system 10 to ensure that the medical image based case is complete. At this step, additional information such as LIS information 655 may be uploaded to the collaboration server 40 and included with the medical image based case. In one embodiment, this review can be conducted by an operator at the requesting system 10.

Similarly, the collaboration server 40 next receives a consult request in step 670 from the requesting system 10 and solely or interactively with the requesting system 10 searches a directory of consulting systems to identify one or more consulting systems appropriate for the particular medical image based case. Note that at this step during the workflow, additional information such as LIS information 655 may be added to the medical image base case.

In step 675 the collaboration server 40 assigns a consulting system 30 to the medical image based case and in one embodiment the medical image based case information is exported to an LIS system managed and maintained by the consulting system 30. Next in step 680, the consulting system 30 analyzes the medical image based case information received from the collaboration server 40 and prepares a consultant analysis and sends the consultant analysis to the collaboration server 40 for storage with the medical image based case. In one embodiment, a companion LIS report or other reports from the consulting system 30 may be included with the consultant analysis and ultimately made part of the medical image based case. The collaboration server 40 then provides the consultant analysis to the requesting system 10 to complete the collaboration workflow. Advantageously, additional digital medical images may be digitized and uploaded simultaneously or serially to provide larger scale collaboration between one or more requesting systems 10 and one or more consulting systems 30.

Additionally, in one embodiment, during the consulting system 30 review, the consulting system 30 may request that additional information be included with the medical image based case. In response, the collaboration server 40 may update the status of the medical image based case and send a notice to the requesting system 10 regarding the request for additional information. Once the requesting system 10 has provided the additional information, the collaboration server 40 may again update the status of the medical image based case and notify the consulting system 30 that the updated medical image based case is ready for review by the consulting system 30. Multiple iterations of requests for additional information may be employed in order to ensure that the medical image based case is complete.

Figure 10:
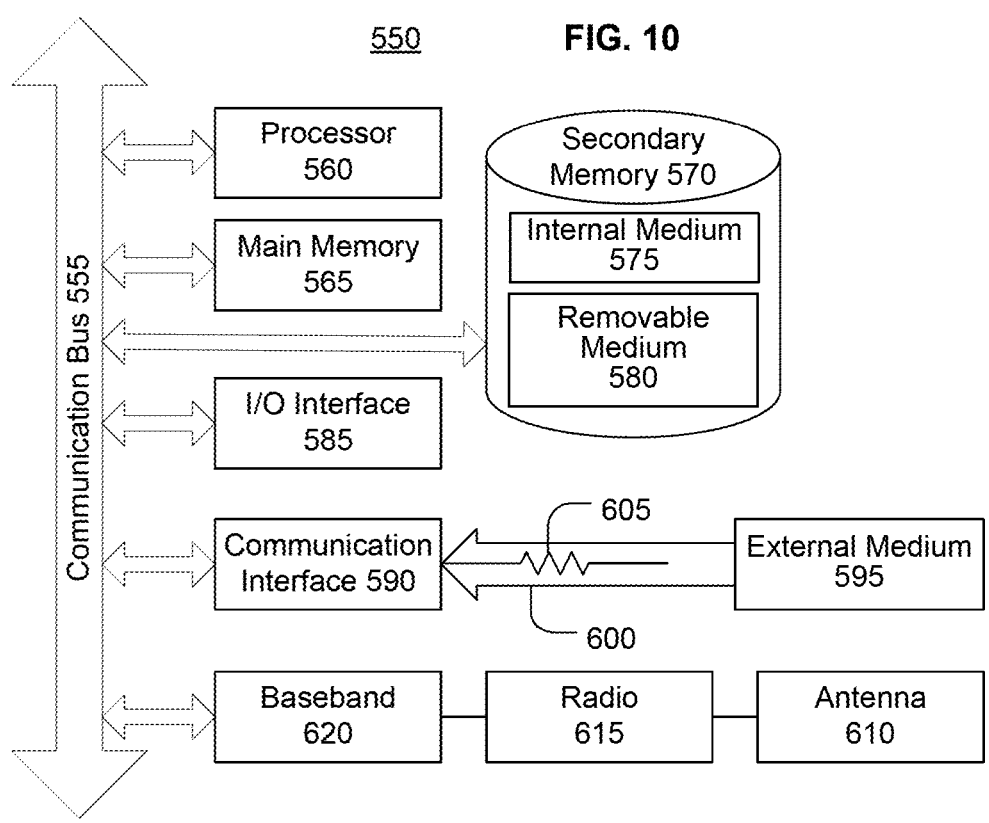
FIG. 10 is a block diagram illustrating an example wired or wireless processor enabled device that may be used in connection with various embodiments described herein.

FIG. 10 is a block diagram illustrating an example wired or wireless system 550 that may be used in connection with various embodiments described herein. For example the system 550 may be used as or in conjunction with a requesting system, consulting system, medical image capture device, smart medical image capture device, server or repository as previously described with respect to FIGS. 1-3. The system 550 can be a personal computer, computer server, personal digital assistant, smart phone, tablet computer or the like, a medical image capture system such as a digital slide scanning system, radiology imaging system, magnetic resonance imaging system, computed axial tomography system, X-ray system or the like or any other processor enabled device that is capable of wired or wireless data communication. Other computer systems and/or architectures may be also used, as will be clear to those skilled in the art. Specialty components needed for specific purposes such as medical imaging can be integrated into the system 550 as will be understood by those skilled in the art and will therefore not be described here in detail. One example of a digital slide scanning system is described in U.S. Pat. No. 6,711,283, which is incorporated herein by reference in its entirety.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A method comprising using at least one hardware processor to:

receive a request to create a medical case from a requesting system over at least one network;
in response to the request,
  create the medical case,
    define a minimum dataset required for the medical case to be complete by performing acts comprising selecting the minimum dataset from a plurality of available minimum datasets based on a medical condition associated with the medical case,
    in advance of capturing medical image data to be included in the medical case, determine one or more image-capture parameters for the medical case, and
    send one or more commands, over the at least one network, to a smart image-capture device at the requesting system, to
      configure the smart image-capture device according to the one or more image-capture parameters, and
      control the smart image-capture device to auto-load and scan a microscope slide, associated with the medical case, to capture the medical image data according to the one or more image-capture parameters;
receive the captured medical image data from the requesting system over the at least one network;
store the medical image data in association with the medical case; and
provide access to the medical case to one or more consulting systems.

2. The method of claim 1, wherein the smart image-capture device is a digital pathology system that captures a whole slide image as the medical image data.

3. The method of claim 1, further comprising using the at least one hardware processor to determine when the medical case is complete based on the minimum dataset, wherein the one or more consulting systems are provided access to the medical case only after the medical case is determined to be complete.

4. The method of claim 1, further comprising using the at least one hardware processor to, after providing access to the medical case to one or more consulting systems, receive analysis information from at least one of the one or more consulting systems.

5. The method of claim 4, further comprising using the at least one hardware processor to, after receiving the analysis information, store the analysis information in association with the medical case.

6. The method of claim 5, further comprising using the at least one hardware processor to provide access to the analysis information to the requesting system.

7. The method of claim 5, further comprising using the at least one hardware processor to, after receiving the analysis information:
determine whether the medical case meets one or more predetermined criteria;
and,
when determining that the medical case meets the one or more predetermined criteria, transmitting the medical case, including the medical image data and the analysis information, to an online training and education repository.

8. The method of claim 1, wherein the one or more image-capture parameters comprise a magnification level.

9. The method of claim 1, further comprising using the at least one hardware processor to provide access to a directory of available consulting systems to the requesting system.

10. The method of claim 1, further comprising using the at least one hardware processor to receive metadata from the requesting system over the at least one network.

11. The method of claim 10, wherein the metadata comprises patient-specific data for a patient from which a sample on the microscope slide was obtained.

12. The method of claim 11, wherein the patient-specific data comprises a laboratory information system (LIS) number, wherein the method further comprises using the at least one hardware processor to assign a case number to the medical case, and wherein the case number comprises the LIS number.

13. The method of claim 10, wherein the metadata identifies a preferred consulting system, and wherein the one or more consulting systems, to which access to the medical case is provided, comprise the preferred consulting system.

14. A non-transitory computer-readable medium having instructions stored thereon, wherein the instructions, when executed by a processor, cause the processor to:
receive a request to create a medical case from a requesting system over at least one network;
in response to the request,
  create the medical case,
    define a minimum dataset required for the medical case to be complete by performing acts comprising selecting the minimum dataset from a plurality of available minimum datasets based on a medical condition associated with the medical case,
    in advance of capturing medical image data to be included in the medical case, determine one or more image-capture parameters for the medical case, and
    send one or more commands, over the at least one network, to a smart image-capture device at the requesting system, to
      configure the smart image-capture device according to the one or more image-capture parameters, and
      control the smart image-capture device to auto-load and scan a microscope slide, associated with the medical case, to capture the medical image data according to the one or more image-capture parameters;
receive the captured medical image data from the requesting system over the at least one network;
store the medical image data in association with the medical case; and
provide access to the medical case to one or more consulting systems.

15. A system comprising:
at least one hardware processor; and
one or more server software modules that are configured to, when executed by the at least one hardware processor,
  receive a request to create a medical case from a requesting system over at least one network,
  in response to the request,
    create the medical case,
      define a minimum dataset required for the medical case to be complete by performing acts comprising selecting the minimum dataset from a plurality of available minimum datasets based on a medical condition associated with the medical case,
      in advance of capturing medical image data to be included in the medical case, determine one or more image-capture parameters for the medical case, and send one or more commands, over the at least one network, to a smart image-capture device at the requesting system, to
configure the smart image-capture device according to the one or more image-capture parameters, and
control the smart image-capture device to auto-load and scan a microscope slide, associated with the medical case, to capture the medical image data according to the one or more image-capture parameters,
receive the captured medical image data from the requesting system over the at least one network,
store the medical image data in association with the medical case, and
provide access to the medical case to one or more consulting systems.

16. The system of claim 15, further comprising the smart image-capture device, wherein the smart image-capture device comprises:
at least one hardware processor; and
one or more client software modules that are configured to, when executed by the at least one hardware processor of the smart image-capture device,
receive the one or more commands from the one or more server software modules over the at least one network,
configure the smart image-capture device and capture the medical image data according to the one or more commands, and
upload the medical image data to the one or more server software modules over the at least one network.

17. The system of claim 16, wherein the one or more client software modules are further configured to:
retrieve information for the medical case from one or more sources; and
upload the information to the one or more server software modules, over the at least one network, as metadata.

18. The system of claim 17, wherein the one or more sources comprise a laboratory information system (LIS).

* * * * *